United States Patent
Pearson et al.

(10) Patent No.: US 10,307,532 B2
(45) Date of Patent: Jun. 4, 2019

(54) INFUSION SITE INTERFACES AND INSERTION DEVICES FOR INFUSION SITE INTERFACES

(71) Applicant: Roche Diabetes Care, Inc., Indianapolis, IN (US)

(72) Inventors: Allen John Pearson, Wistow Huntingdon (GB); James Terence Collins, Peterborough (GB); Neil Alexander Pryor, Bristol (GB)

(73) Assignee: Roche Diabetes Care, Inc., Indianapolis ( * ) Notice: Subject to any disclaimer, the term of this patent is extended or adjusted under 35 U.S.C. 154(b) by 0 days.

(21) Appl. No.: 15/424,032

(22) Filed: Feb. 3, 2017

(65) Prior Publication Data
US 2017/0189611 A1  Jul. 6, 2017

Related U.S. Application Data

(60) Division of application No. 13/714,239, filed on Dec. 13, 2012, now Pat. No. 9,592,338, which is a
(Continued)

(30) Foreign Application Priority Data

Jun. 18, 2010  (EP) ..................................... 10166528
Jun. 18, 2010  (EP) ..................................... 10166531

(51) Int. Cl.
*A61M 5/158* (2006.01)
*A61M 25/06* (2006.01)
(Continued)

(52) U.S. Cl.
CPC ............ *A61M 5/158* (2013.01); *A61M 5/142* (2013.01); *A61M 5/1626* (2013.01);
(Continued)

(58) Field of Classification Search
CPC .... A61M 5/158; A61M 5/1626; A61M 5/142; A61M 2005/1586; A61M 2005/1587; A61M 2005/1585
See application file for complete search history.

(56) References Cited

U.S. PATENT DOCUMENTS

2002/0173769 A1*  11/2002  Gray ................... A61M 5/1456
604/506
2003/0181874 A1  9/2003  Bressler et al.
(Continued)

FOREIGN PATENT DOCUMENTS

| EP | 1 820 525 A1 | 8/2007 |
|---|---|---|
| WO | WO 2002/07804 A1 | 1/2002 |
| WO | WO 2008/092782 A1 | 8/2008 |

*Primary Examiner* — Amber R Stiles
(74) *Attorney, Agent, or Firm* — Woodard, Emhardt, Henry, Reeves & Wagner, LLP

(57) ABSTRACT

A device for inserting an infusion cannula, or sensor, into a patient is presented. The device comprises an insertion needle removable within the infusion cannula, a handle connected to the insertion needle, and a needle cover. The needle cover pivotably mounted on the handle is rotatably movable between a first position, i.e., the front of the insertion needle is in the needle cover, and a second position, i.e., the front is exposed. An infusion site interface comprises a body mounted on a pad attached to the patient; an infusion cannula for inserting into the patient that is connected to the body; a cavity within the body fluidly connected to the cannula; and a septum that seals closed the cavity. The septum is penetrable by an insertion needle in the infusion cannula and by a hollow needle of an infusion tubing connector coupled to the infusion site interface.

23 Claims, 17 Drawing Sheets

Related U.S. Application Data continuation of application No. PCT/EP2011/059654, filed on Jun. 10, 2011.

(51) Int. Cl.
　　*A61M 5/142*　　　(2006.01)
　　*A61M 39/02*　　　(2006.01)
　　*A61M 5/162*　　　(2006.01)

(52) U.S. Cl.
　　CPC .... *A61M 25/0612* (2013.01); *A61M 25/0631* (2013.01); *A61M 39/02* (2013.01); *A61M 25/0606* (2013.01); *A61M 2005/1585* (2013.01); *A61M 2005/1586* (2013.01); *A61M 2005/1587* (2013.01)

(56) References Cited

U.S. PATENT DOCUMENTS

| | | | |
|---|---|---|---|
| 2005/0101932 A1* | 5/2005 | Cote | A61M 5/158 604/506 |
| 2005/0251098 A1* | 11/2005 | Wyss | A61M 5/158 604/263 |
| 2006/0036214 A1 | 2/2006 | Mogensen et al. | |
| 2006/0184104 A1 | 8/2006 | Cheney et al. | |
| 2008/0281270 A1* | 11/2008 | Cross | A61M 5/1413 604/122 |
| 2011/0046564 A1 | 2/2011 | Zhong | |

* cited by examiner

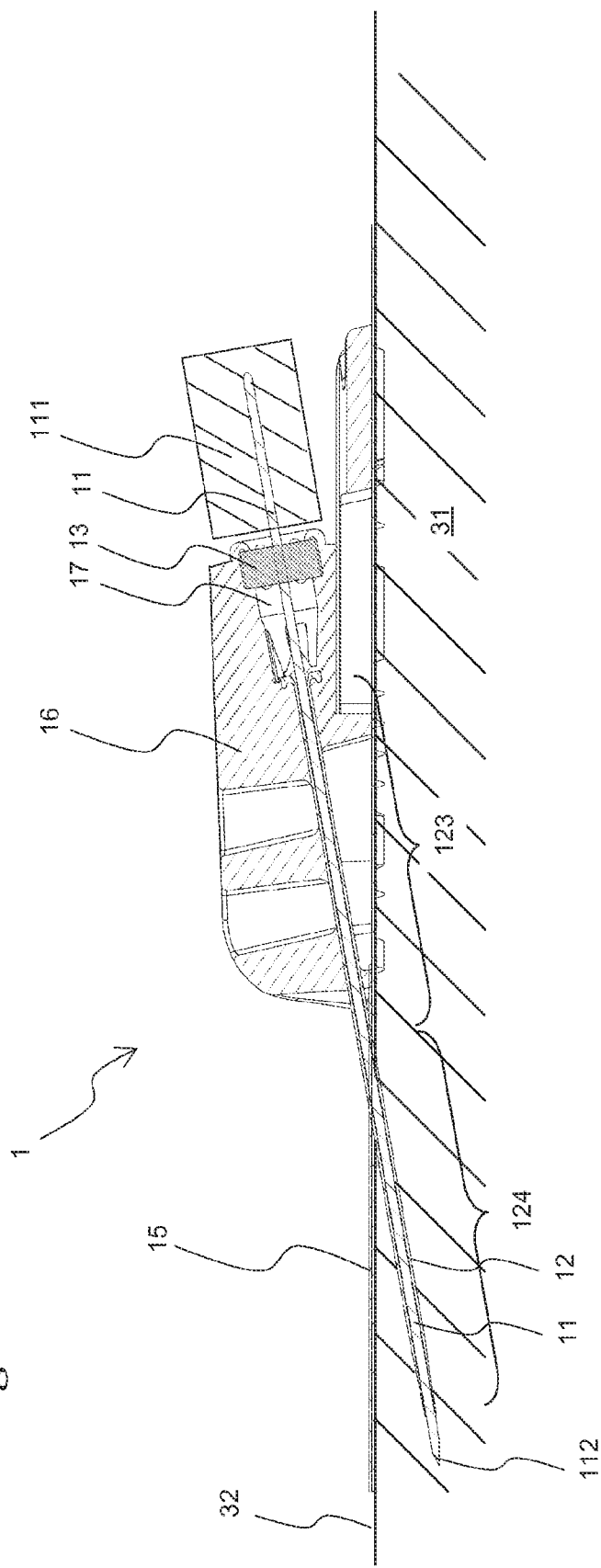

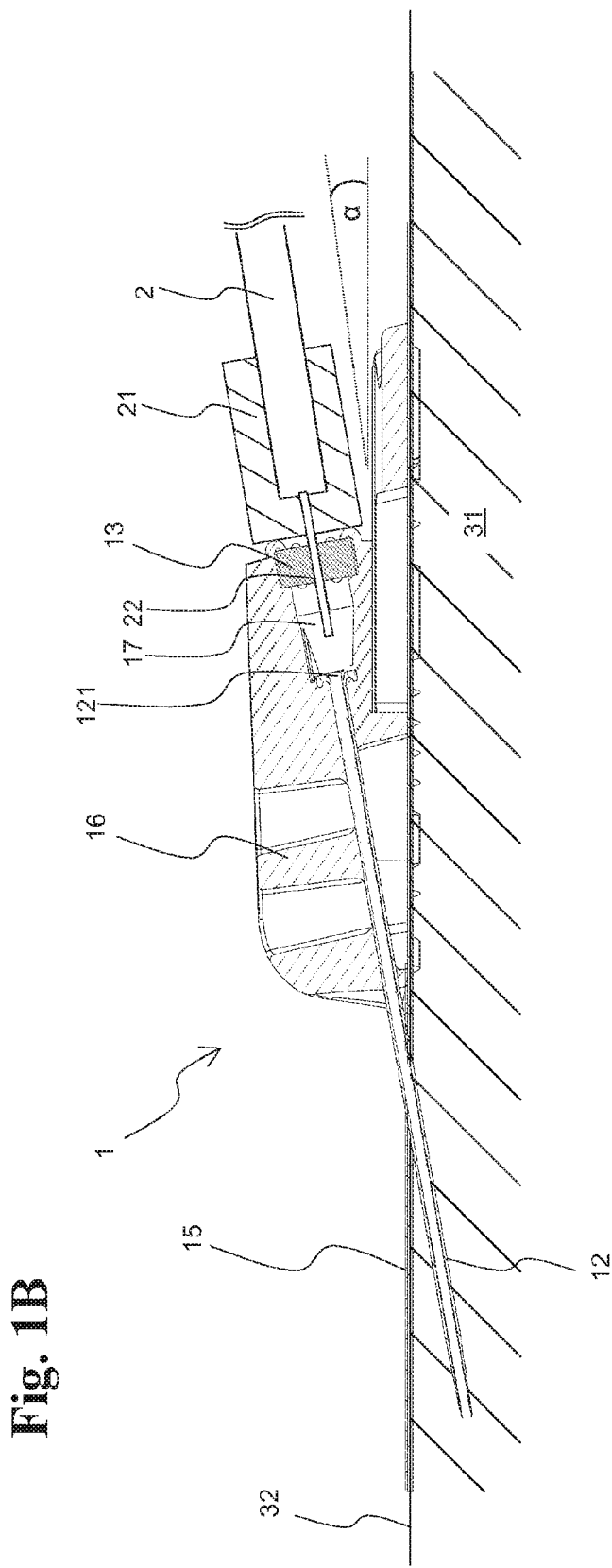

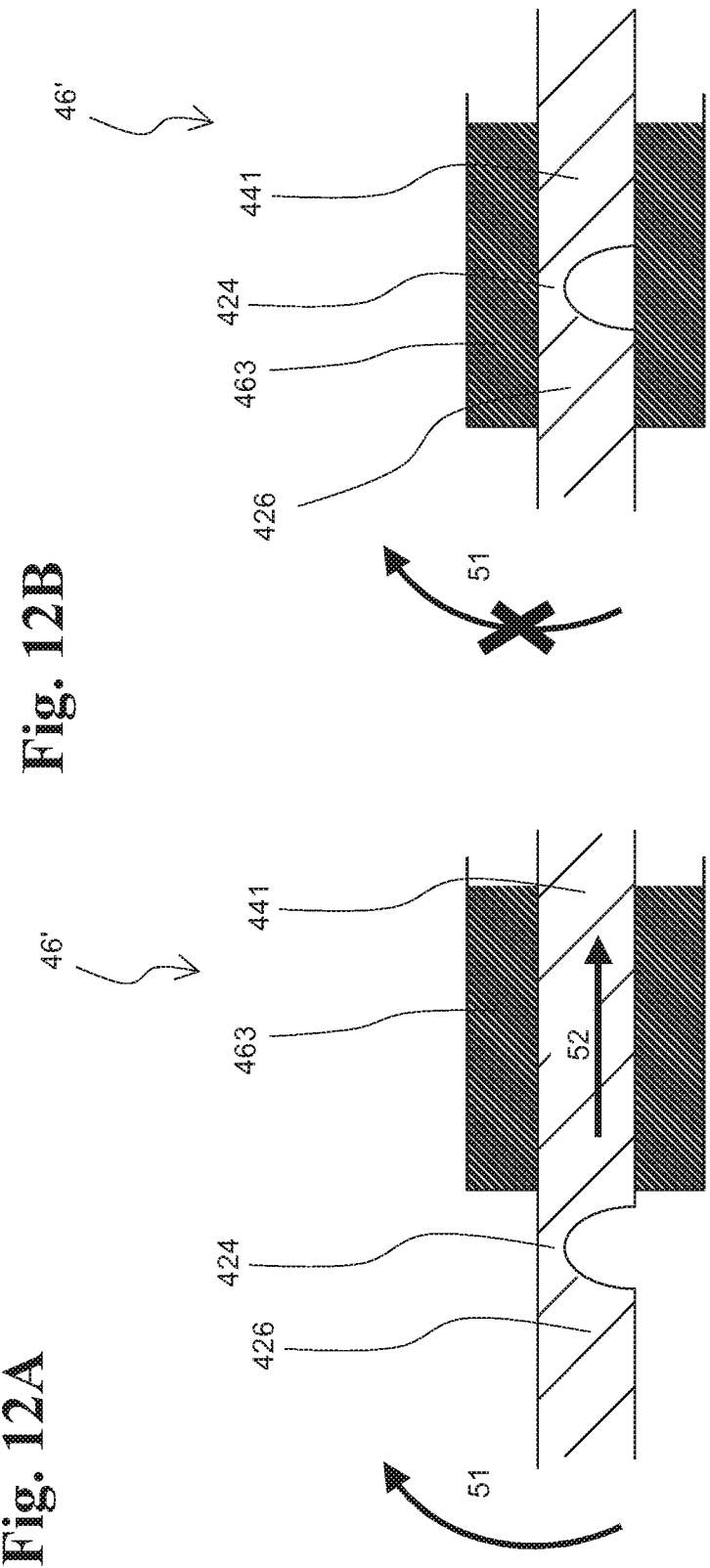

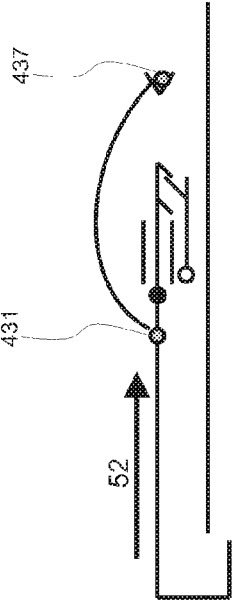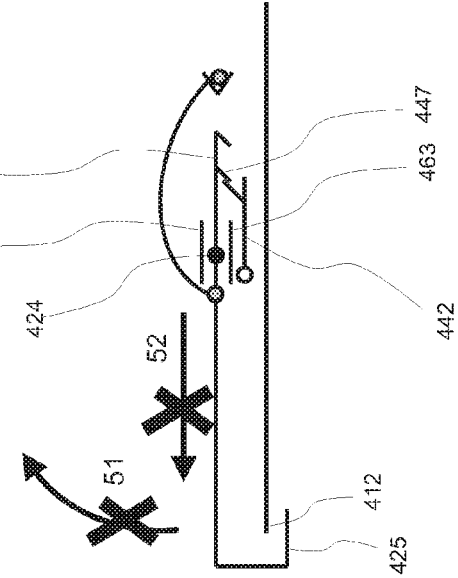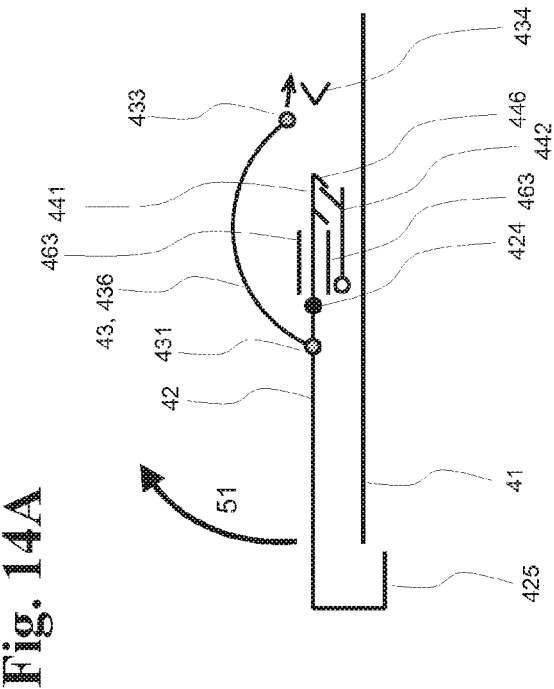

INFUSION SITE INTERFACES AND INSERTION DEVICES FOR INFUSION SITE INTERFACES

CROSS-REFERENCE TO RELATED APPLICATIONS

This application is a divisional of U.S. application Ser. No. 13/714,239, filed Dec. 13, 2012, which is a continuation of International Application No. PCT/EP2011/059654, filed Jun. 10, 2011, which is based on and claims priority to European Application No. 10166528.9, filed Jun. 18, 2010 and European Application No. 10166531.3, filed Jun. 18, 2010, which are hereby incorporated by reference.

BACKGROUND

The present disclosure generally relates to infusion site interfaces with soft infusion cannulas and insertion devices for use with soft infusion cannulas, sensors, and the like, and, in particular, to infusion site interfaces used with infusion pumps and insertion devices for infusion site interfaces used with infusion pumps.

Devices for the automated release of liquid medicines are generally used with patients who have continuous, but varying needs, of a medicine that can be administered by subcutaneous infusion. Specific applications are, for example, certain pain therapies as well as the treatment of diabetes. Infusion pumps are particularly suitable for self-administration of liquid medicine. In such cases, computer controlled infusion pumps are used, which can be carried by on the patient's body and which contain a certain amount of liquid medicine in a medicine reservoir. The medicine reservoir often comprises medicine sufficient for one to several days. The liquid medicine is supplied to the patient's body from the medicine reservoir through an infusion cannula or an injection needle which is commonly placed in the subcutaneous body tissue.

A common type of infusion pump systems for continuous subcutaneous infusion comprises an infusion pump fluidly connected to an infusion set having an infusion site interface and infusion tubing. The infusion pump is attached to a convenient place on the patient's body, or clothes, and the infusion tubing is fluidly connected to the pump with a suitable connector. The infusion site interface is placed at a suitable position on the body, often in the abdominal region around and below the navel. Other possible infusion sites include upper leg, upper buttocks, hips, upper arms and lower back. The infusion site interface contains an infusion cannula inserted into the subcutaneous tissue of the patient. The infusion cannula can be a rigid, or semi-rigid, hollow needle or as a soft, flexible cannula, for example in the form of a PTFE cannula. Soft cannulas are generally preferred. To avoid medical problems such as infections, the infusion site interface has to be regularly replaced, usually after a few days.

Soft infusion cannulas are well known for both intravenous and subcutaneous infusion. A rigid insertion needle arranged inside the soft cannula facilitates penetration of the skin of the patient and insertion of the cannula into the body tissue. Likewise, hollow sensors for measuring an analyte such as, for example, glucose are known. After the infusion cannula, or the sensor, has been placed, the insertion needle is removed from the cannula, or sensor, while the soft cannula or sensor remains in the body tissue.

The infusion cannula can be inserted perpendicular to the body surface or at an angle.

Infusion site interfaces with angled cannulas can have the advantage that the needle may be easily manually inserted in the body tissue using the same technique as for standard injection needles. Furthermore, the part of the cannula placed in the body can be longer for obtaining a certain infusion depth which can lower the risk of the cannula accidentally leaving the body tissue during movements of the patient.

FIGS. 1A and 1B depict an example of a known infusion site interface 1 with angled infusion cannula 12, which is similar to an infusion site interface of WO 02/07804 A1 which is hereby incorporated by reference. Another similar infusion site interface is part of an infusion set distributed by Roche Diabetes Care AG, Burgdorf, Switzerland, under the name ACCU-CHECK® TENDERLINK®.

Other types of known infusion site interfaces comprise two separate septums. One septum is used to seal closed the cavity when the insertion needle is removed from the cannula and a second septum is used to fluidly connect the cavity with infusion tubing or a pump system via a hollow needle penetrating the second septum. Generally, such arrangements are used for infusion site interfaces with cannulas that penetrate the skin perpendicularly. Thus, the first septum is arranged collinear with the perpendicular insertion needle. The second septum is arranged in a right angle to the first septum, in order to allow attaching a connecting infusion tubing horizontally, parallel to the adhesive pad and the patient's skin.

The manufacture of infusion site interfaces with two septums is typically more expensive than with one septum because the injection molding is more complicated. In addition, such interfaces have a higher overall height which increases the risk of the infusion site interface getting caught on clothes. Furthermore, the volume of the cavity in the interface may have to be larger for geometrical reasons. Volumes in the fluid path that cannot be emptied (the so-called dead volume), such as the volume of the cavity, are preferred to be as small as possible in infusion pump applications.

Many diabetic patients attach the infusion site interface and insert the infusion cannula, or sensor, themselves. However, even with extensive training, the handling of sharp, pointed needles unavoidably poses a risk of injuries for patients, as well as medical personnel. In addition, inappropriate disposal of used, and thus contaminated, insertion needles represents a health risk for third persons, for example, small children. While suitable disposable containers for used needles are generally available in medical facilities, self-care patients typically do not have them and have to dispose the insertion needle together with normal household waste.

Therefore, there is a need for devices for inserting cannulas and sensors and for interfaces having such cannulas and sensors, that allow easy and safe handling by both medical personnel and patients, and that can be safely disposed after use. Furthermore there is a need for infusion site interfaces that allow easy and safe use, have a low profile, and are less prone to accidentally catching on clothing, obstacles or the like.

SUMMARY

According to the present disclosure, a device for inserting an infusion cannula and/or a sensor into a body of a patient is presented. The device comprises an insertion needle that is removably arranged in the infusion cannula and/or sensor, a handle structure connected to the insertion needle, and a needle cover. The needle cover is pivotably mounted on the handle structure and is rotatably movable between a first position, where a front part of the insertion needle is located in the needle cover, and a second position, where the front part of the insertion needle is exposed.

In accordance with one embodiment of the present disclosure, an infusion site interface is presented. The infusion site interface comprises an interface body mounted on a pad adhesively attached to a body of a patient, a soft infusion cannula inserted into the body of the patient wherein the cannula is connected to the interface body, a cavity within the interface body fluidly connected to the cannula, and a septum that seals closed the cavity. The septum is penetrable by an insertion needle in the infusion cannula, in a first angle ($\beta-\varepsilon$) to its perpendicular, and is penetrable by a hollow needle of an infusion tubing connector coupled to the infusion site interface, in a second angle ($\varepsilon$) to its perpendicular. The infusion site interface comprises a guide to guide the hollow needle of the connector during coupling, parallel to a plane defined by the pad.

Accordingly, it is a feature of the embodiments of the present disclosure to have devices for inserting cannulas and sensors and to have interfaces having such cannulas and sensors, that allow easy and safe handling by both medical personnel and patients, and that can be safely disposed after use. It is also a feature of the embodiments of the present disclosure to have infusion site interfaces that allow easy and safe use, have a low profile, and are less prone to accidentally catching on clothing, obstacles or the like. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 1A illustrates a cross-section through an infusion site interface with angled infusion cannula, attached to the body of a patient, directly after insertion of the infusion cannula.

FIG. 1B illustrates a cross-section through an infusion site interface with angled infusion cannula, attached to the body of a patient, after removal of the insertion needle and with established fluid connection to an infusion tubing according to the prior art.

FIG. 12A illustrates a second rotational lock mechanism according to an embodiment of the present disclosure in a first position.

FIG. 12B illustrates the second rotational lock mechanism in a second position.

FIGS. 14A-D schematically illustrates the different positions of the needle cover in regard to the handle of the device according to an embodiment of the present disclosure.

FIG. 14A schematically illustrates the needle cover in a first position.

FIG. 14B schematically illustrates the needle cover in a second position.

FIG. 14C schematically illustrates the needle cover pivoted back to the first position.

FIG. 14D schematically illustrates the needle cover in a third position.

FIG. 17A schematically illustrates a first variant.

FIG. 17B schematically illustrates a second variant.

FIG. 17C schematically illustrates a third variant.

FIG. 17D schematically illustrates a fourth variant.

DETAILED DESCRIPTION

Figure 2:
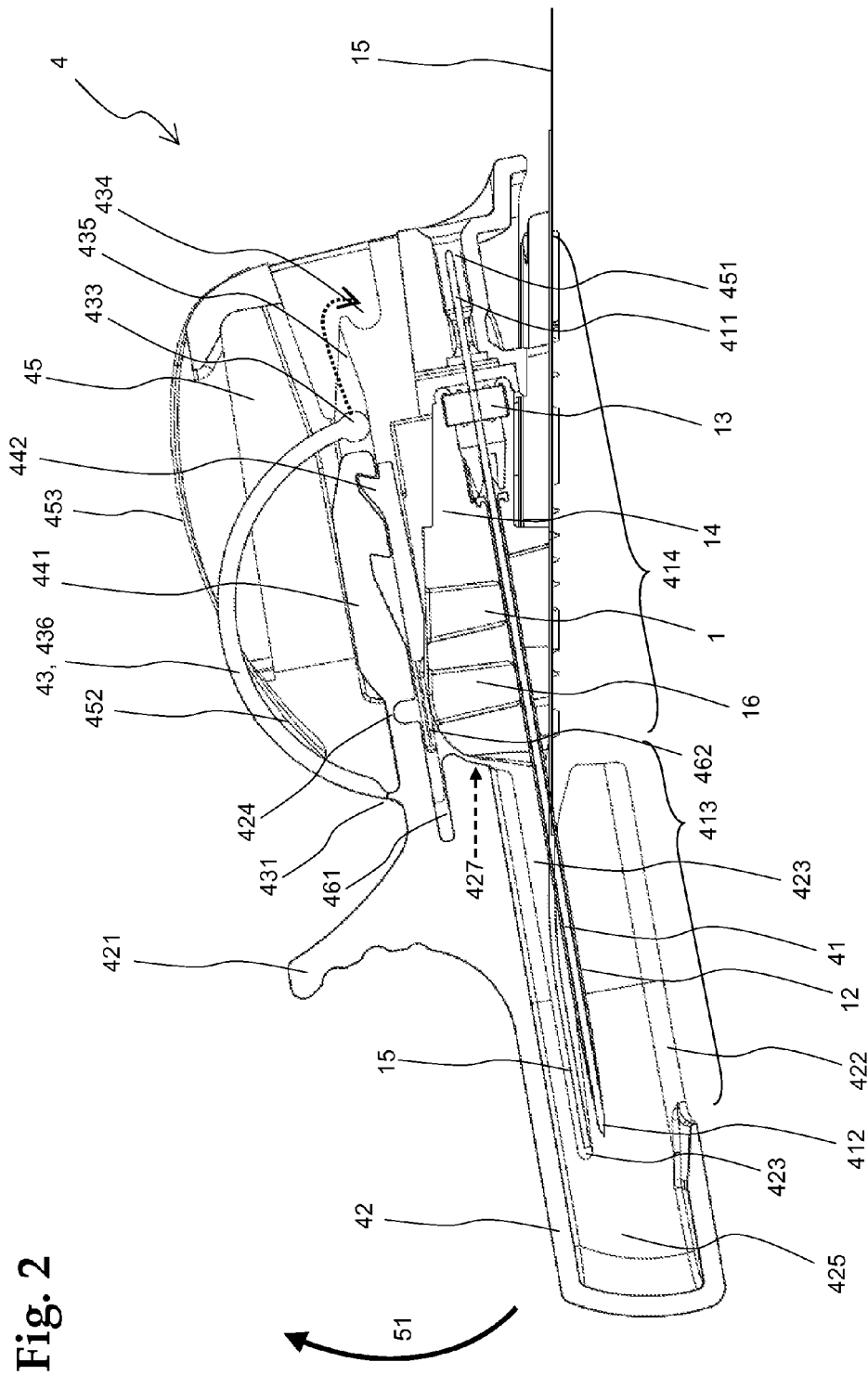
FIG. 2 illustrates a cross-section of a cannula insertion device attached to an infusion site interface with a soft cannula, prior to first application where the needle cover is in a first position, with the needle located inside the needle cover according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The term 'user' can mean signify a person that is using the device, while the term 'patient' can mean the subject to whom the device is applied. The subject can be a human, but also an animal. In the case of self-administration, the user and the patient are identical.

A device according to the present disclosure for inserting an infusion cannula and/or a sensor into a body of a patient can comprise an insertion needle that can be removably arranged in the infusion cannula and/or sensor, a handle structure connected to the insertion needle, and a needle cover. The needle cover can be pivotably mounted on the handle structure and can be rotatably movable between a first position, where a front part of the insertion needle is located in the needle cover, and a second position, where the front part of the insertion needle is exposed. Advantageously, the needle cover can comprise a longitudinal slot that can be arranged such that the front part of the insertion needle can pass through the slot when the needle cover is pivoted.

In one embodiment, the device can comprise a lock mechanism for locking the needle cover in the second position.

In another embodiment, the device can comprise a spring element to actuate the needle cover toward the second position. The spring element can comprise an elastic bar that is connected on one end with the needle cover by a first hinge and is connected on the other end with the handle structure by a second hinge. In this embodiment, when the spring element in a first configuration is non-functional, in a second configuration, the spring element can actuate the needle cover toward the second position. The spring element can irreversibly change from its first configuration to its second configuration when the needle cover arrives at the second position for the first time. In another embodiment, the spring element in its first configuration can actuate the needle cover toward the first position.

In one embodiment, one end of the spring element bar can comprise a pawl that can irreversibly snap into a groove in the handle structure when the needle cover arrives at the second position, thereby establishing a second hinge between the end of the bar and the handle structure. The needle cover can comprise an element slidably mounted on the handle structure, such that the needle cover with the sliding element can linearly be moved between the first position and a third position.

In one embodiment, the device can comprise one or more lock mechanisms for locking the needle cover in a position where the needle is located within the needle cover.

In another embodiment, the needle cover can comprise an element that can be slidably mounted on the handle structure and can be linearly movable between the first position and a third position. A rotational lock mechanism can be a slot-tongue joint, wherein a slot can be on the cover and the tongue can be on the sliding element, or vice versa. The slot and the tongue may not engage when the sliding element is in one position, and may engage when the sliding element is in the other position, thereby blocking the rotational motion of the needle cover and establishing a lock of the needle cover.

In a further embodiment, the needle cover can comprise an element that can be slidably mounted on the handle structure and can be linearly movable between the first position and a third position. A rotational lock mechanism can comprise a guiding slot. The hinge of the needle cover can be located outside the guiding slot when the sliding element is in one position and can be located inside the guiding slot when the sliding element is in the other position, thereby blocking the rotational motion of the needle cover by making the hinge non-functional, and establishing a lock of the needle cover in the first position.

In another embodiment, the needle cover can comprise an element that can be slidably mounted on the handle structure such that the needle cover with the sliding element can be linearly movable between the first position and a third position. A translational lock mechanism can be a linear ratchet mechanism. The sliding element can act as a linear rack element of the linear ratchet mechanism and the handle structure can comprise a spring loaded pawl of the linear ratchet mechanism, or vice versa. In one embodiment, the needle cover can comprise a closed cap that can be arranged such that the tip of the insertion needle can be within the cap when the sliding element is in the third position, thereby positively locking the needle within the cap.

In yet another embodiment, the needle cover can comprise two parallel slots in the two sidewalls of the cover. This can provide the possibility that an adhesive pad of an infusion site interface can be within these two slots.

An infusion site interface and a sensor site interface can comprise an insertion device as discussed above, wherein an insertion needle of the insertion device can be in an infusion cannula and/or a sensor of the infusion site interface.

Such an infusion site interface and/or sensor site interface can comprise a soft infusion cannula and/or sensor, an insertion needle removably arranged in the infusion cannula and/or sensor, a handle structure connected to the insertion needle, and a needle cover. The needle cover can be pivotably mounted on the handle structure and can be rotatably moved between a first position, where a front part of the insertion needle is located in the needle cover, and a second position, where the front part of the insertion needle is exposed.

An infusion set and an infusion pump system can comprise an insertion device, or an infusion site interface, respectively.

An infusion site interface can comprise an interface body mounted on a pad adhesively attached to a body of a patient; a soft infusion cannula inserted into the body of the patient, wherein the cannula can be connected to the interface body; a cavity arranged within the interface body, fluidly connected to the cannula; and one single septum that seals closed the cavity. The single septum can be penetrable by an insertion needle arranged in the infusion cannula, in a first angle β–ε to its perpendicular, and can be penetrable by a hollow needle of an infusion tubing connector coupled to the infusion site interface, in a second angle ε to its perpendicular. The infusion site interface can comprise a guide that guides the hollow needle of the connector during coupling, parallel to a plane defined by the pad. Such an interface device can comprise an insertion needle arranged in the infusion cannula and penetrating the septum.

Surprisingly it can be possible to use one single septum for both the insertion needle and the hollow needle of the connector, although the two needles are not collinear to each other. Thus, one single septum can be used for both needles. At the same time the hollow needle, and thus also the connector and the adjacent tubing, can be parallel to the plane defined by the pad of the interface allowing for a low profile of the interface with coupled connector.

In one exemplary embodiment, an infusion site interface can comprise an insertion device, wherein the insertion needle of the insertion device can be arranged in the infusion cannula of the infusion site interface. An infusion set and an infusion pump system can comprise an infusion site interface.

Figure 4:
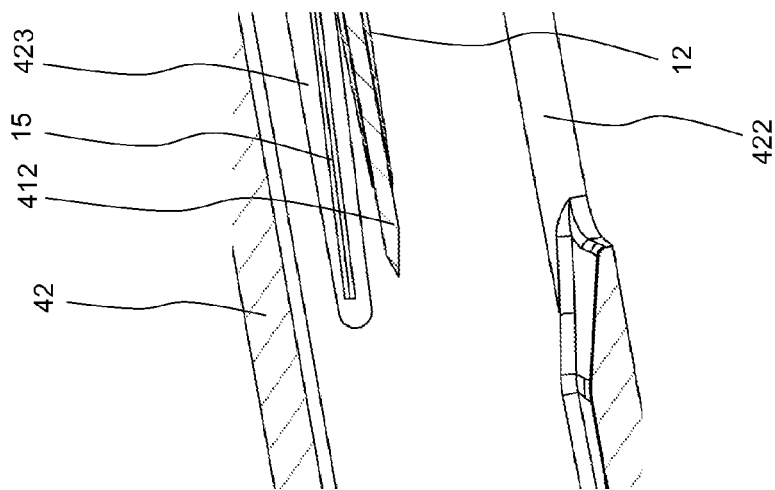
FIG. 4 illustrates a detail view of the device in FIG. 2 in the area of the needle tip according to an embodiment of the present disclosure.

An embodiment of a device 4 for inserting a soft cannula 12 into body tissue is shown in a cross-sectional view in FIG. 2. Different detail views of the embodiment are provided in FIGS. 3, 4, and 5. The disclosed device 4 can be particularly suitable for application with an infusion site interface 1 as shown in FIG. 1A and is shown already coupled to an infusion site interface 1. The insertion device 4 in combination with the infusion site interface 1 represents an embodiment of an infusion site interface.

The infusion site interface 1 shown in FIG. 2 is an infusion site interface 1 with one single septum 13, as well as a guide 14 that can allow a hollow needle of a tubing connector to penetrate the septum 13 parallel to the plane defined by the pad 15 (horizontal in FIG. 2) with an angle in regard to the axis of the septum 13 and the cannula 12. However, an insertion device 4 can also be used in combination with a prior art infusion site interface 1, as for example the embodiment shown in FIGS. 1A and 1B.

Figure 6:
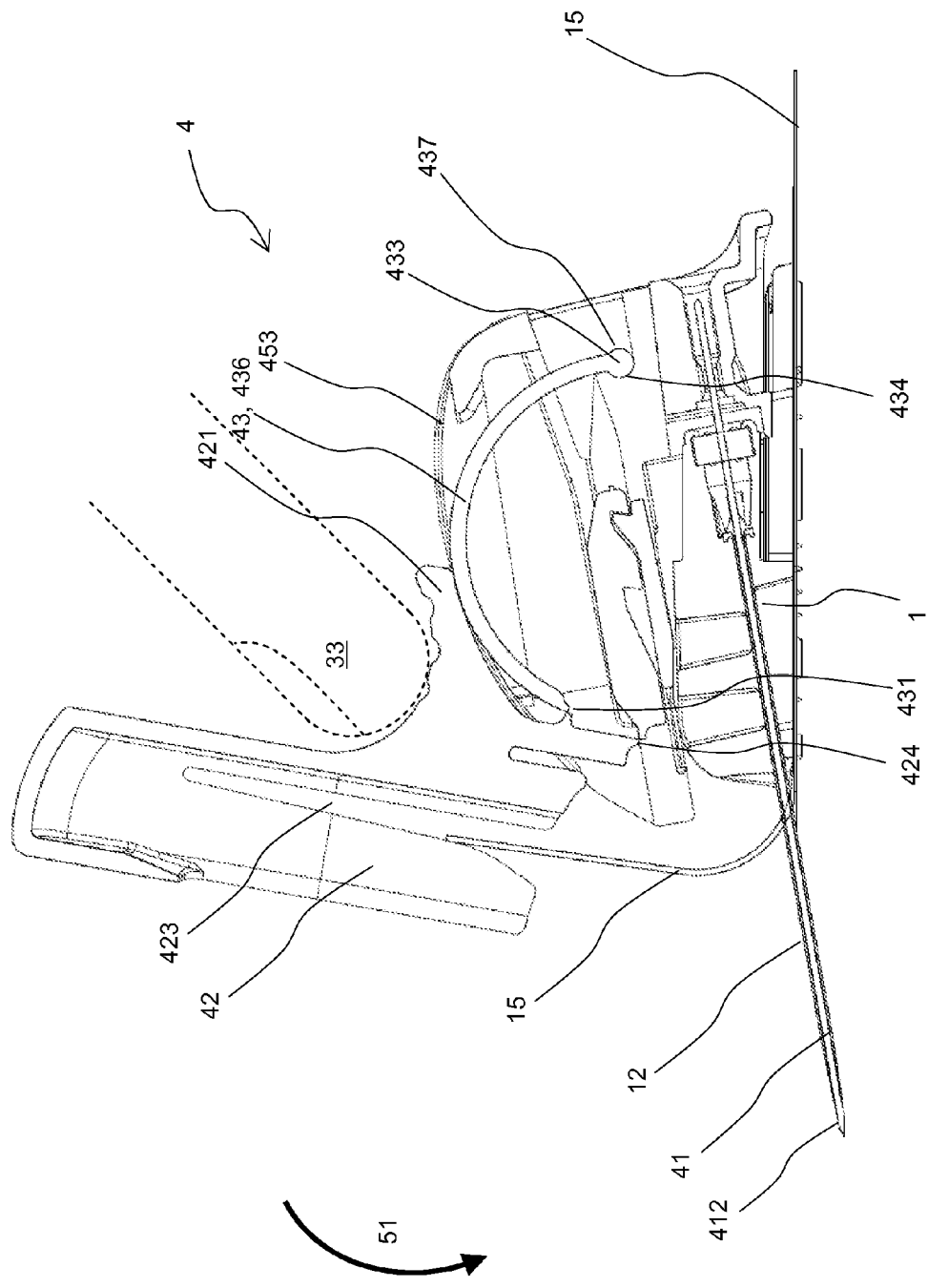
FIG. 6 illustrates a cross-section of the device of FIG. 2, with the needle cover in a second, tilted position, in which the needle with surrounding cannula lies free and can be inserted into the body of a patient according to an embodiment of the present disclosure.

The insertion device 4 is shown in a form as it is provided to a user prior to first use, already assembled with an infusion site interface 1. The device 4 can comprise an insertion needle 41 arranged in the infusion cannula 12 of the infusion site interface 1, a handle structure 45 connected at one end 451 to a first end 411 of the needle 41, and a needle cover 42 pivotably mounted 424 on the handle structure. The needle cover 42 can be a sleeve closed at one end, forming a cap 425, and with a longitudinal access slot 422. The needle cover 42 can be pivoted 51 between a first position and a second position, whereas the insertion needle 41 does not change its position and can pass through the access slot 422 of the needle cover 42. The needle cover 42 can have a grip 421 that allows a user to actuate the needle cover 42 by pulling the grip 421 toward the handle frame 45. In the first position, as it is shown in FIG. 2, the insertion needle 41 with infusion cannula 12 can be located inside the cover 42. The needle tip 412 is not accessible and there is no risk for a user or patient of getting inadvertently stung. In the second position, as shown in FIG. 6, the needle 41 is ready for insertion into the body tissue of a patient.

For being pivotably movable in regard to the frame 45, the needle cover 42 can be connected by hinge 424 to a sliding element 441, slidably mounted in the handle structure 45. The hinge 424 can be a living hinge. The sliding element 441 can be part of a translational lock 44 such as a linear ratchet mechanism, which will be discussed in more detail further below.

A spring element 43 in the form of an unbiased, curved bar 436 can be arranged between the needle cover 42 and the sliding element 441. It can be connected with the needle cover 42 by a first hinge 431, such as a living hinge. On the other end of the curved bar 436, the spring element 43 can comprise a pawl 433. When the needle cover 42 is pivoted toward the second position, the first hinge 431 can bend and the pawl 433 of the spring element 43 can travel on a ramp to the right (dotted arrow in FIGS. 2 and 5). The spring element 43 may not deform or be biased during this rotational movement 51.

Both the first hinge 431 and the needle cover hinge 424 can be living hinges. Prior to the first rotation movement, the living hinges 431, 424 can provide a certain, small resistance that can prevent the needle cover 42 from unwanted rotation during manufacture or handling. The needle tip 412 can remain safely located inside the needle cover 42 and the needle 41 can only be accessible when the user actively actuates the rotational motion 51 of the needle cover 42. After the first rotational actuation, the two hinges 424, 431 do not have such a resistance any more.

In addition to the access slot 422 for the needle 41, the needle cover 42 can furthermore comprises two longitudinal slots 423 on two opposite sides of the needle cover 42. The frontal part of the adhesive pad 15 of the infusion site interface 1 can be arranged in the two slots 423, as is also visible in FIG. 4.

The needle cover 42, the sliding element 441 and the spring element 43 can be formed as one integral part and can be manufactured, for example, by injection molding of a suitable thermoplastic polymer material. The same can apply to the handle structure 45. Prior to assembly, the pawl 433 and the sliding element 441 can be connected by a thin predetermined breaking point, which can protect the living hinges 431, 424 from being bent during manufacture or assembly, and which can be cut during or after assembly of the needle cover 42 and the handle 45. The insertion needle 41 may be a steel rod or a rigid polymer rod.

Figure 7:
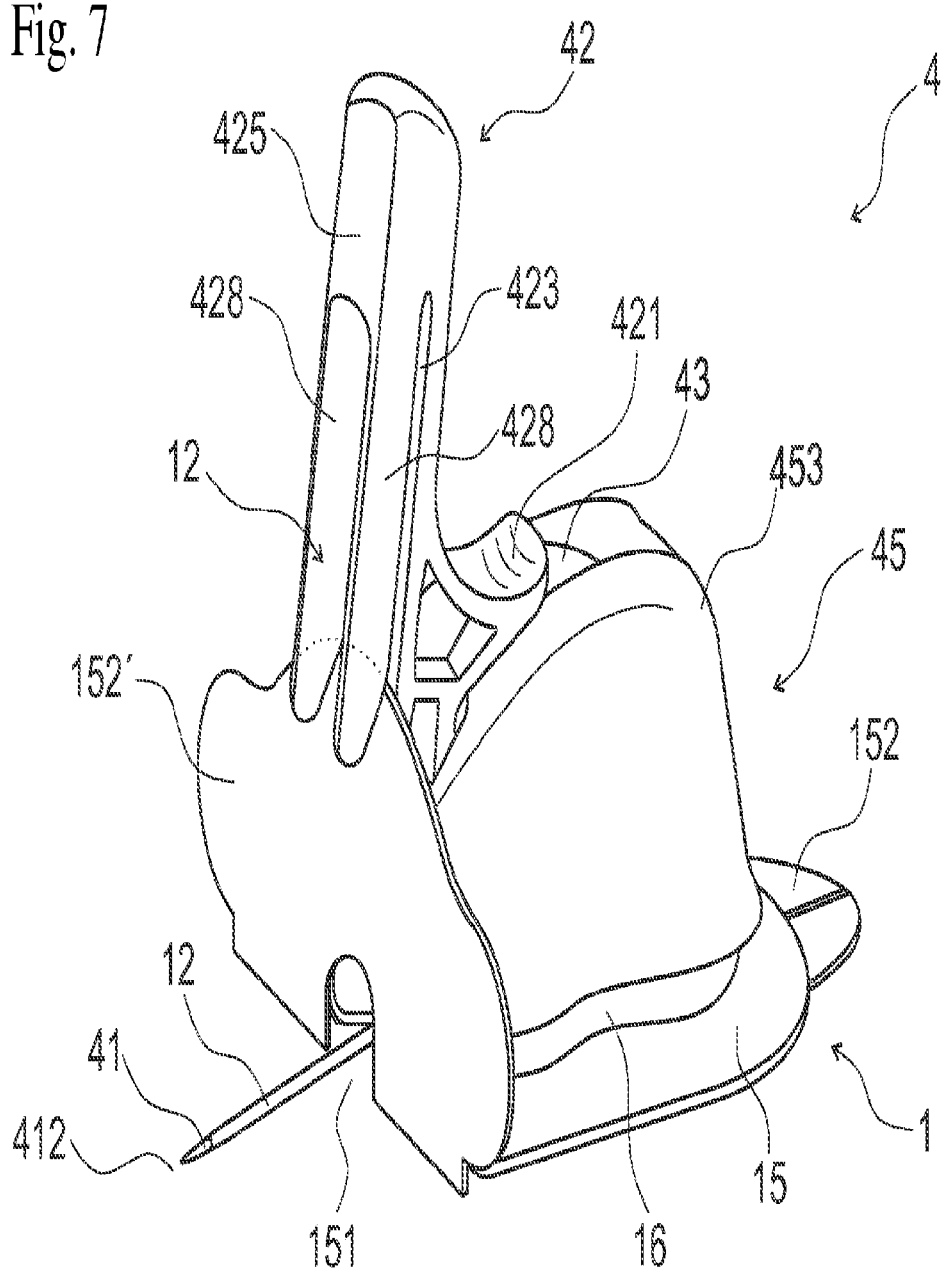
FIG. 7 illustrates a perspective view of the device of FIG. 2, with the needle cover in a second, tilted position, corresponding to FIG. 6 according to an embodiment of the present disclosure.

For inserting the needle 41 with the cannula 12 into the body of a patient, the user can pivot the needle cover 42 back to a second position, as shown in FIGS. 6 and 7. The user can grasp the handle 45 between two fingers (for example thumb and middle finger) and can pull the grip 421 toward the cover 453 of the handle structure 45 with the index finger 33, until the maximum position is reached ("second position of cover"), where the grip touches the cover 453.

During the pivotal motion, the front end of the adhesive pad 15 can slide in the longitudinal slots 423. In the second position, the needle cover 42 can be held by the slots 423 and can be bent upwards. The user can easily see the insertion needle 41, without the need of bending the pad 15 upwards manually. The user can now penetrate the skin 32 of the patient with the now exposed needle 41, and position the needle 41 and cannula 12 within the body tissue.

With the cannula 12 of the interface 1 correctly inserted, the user can then remove the two cover foil parts 152, 152' of the adhesive layer of the pad 15 to adhere the pad to the skin 32 of the patient. After this step, the insertion device 4 can be removed from the infusion site interface 1 by retracting the insertion needle 41 from the cannula 12 of the interface 1. Alternatively the insertion device 4 can be removed first and the cover foil of the adhesive pad 15 removed later.

In the device 4, a mechanism can be provided that can temporarily lock the needle cover 42 in the second, tilted position, which will now be discussed in more detail. Such a lock can have the advantage that the user does not have to constantly press the grip 421 of the needle cover 42, and can more easily remove the device 4 from the interface.

Figure 8:
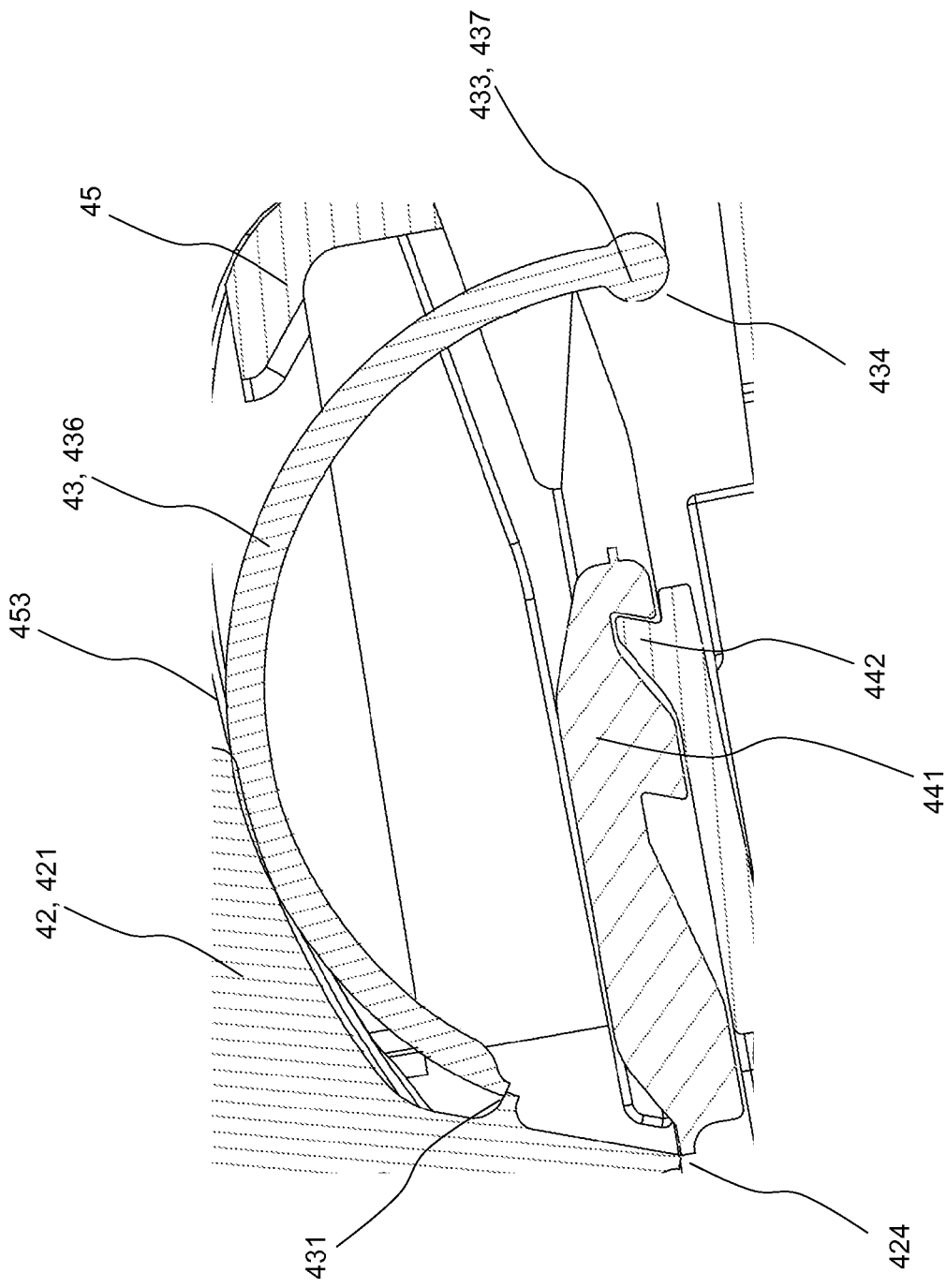
FIG. 8 illustrates a detail view of the spring element in FIG. 6 according to an embodiment of the present disclosure.

Referring back to FIG. 5, one can see the path (dotted arrow) that the pawl 433 of the spring element 43 can take during the first pivotal motion from the first to the second position. The pawl 433 can move to the right, gliding on ramp 435. The pawl 433 can interact with a corresponding groove 434 provided in the handle structure 45. When the pawl 433 reaches the end of the ramp 435, it can snap into the groove 434, permanently establishing a second hinge 437 of the spring element 43, as shown in the detail view in FIG. 8. The spring element 43 can still be unbiased.

For pivoting the needle cover 42 back towards the first position of FIG. 2, the user now has to overcome the spring force of the spring element 43. As a result, the user may release the cover grip 421 without having the needle cover 42 returning to the first position. This can be particularly convenient because the user can change the grip position on the handle structure 45, or can release the handle structure 45 completely.

After the user has positioned the cannula 12 within the body of the patient and, if applicable, has attached the interface 1 to the body of the patient, the user can remove the device 4 from the interface 1 by retracting the insertion needle 41 of the device 4 from the cannula 12, the needle cover 42 still being in the tilted, second position.

Figure 9:
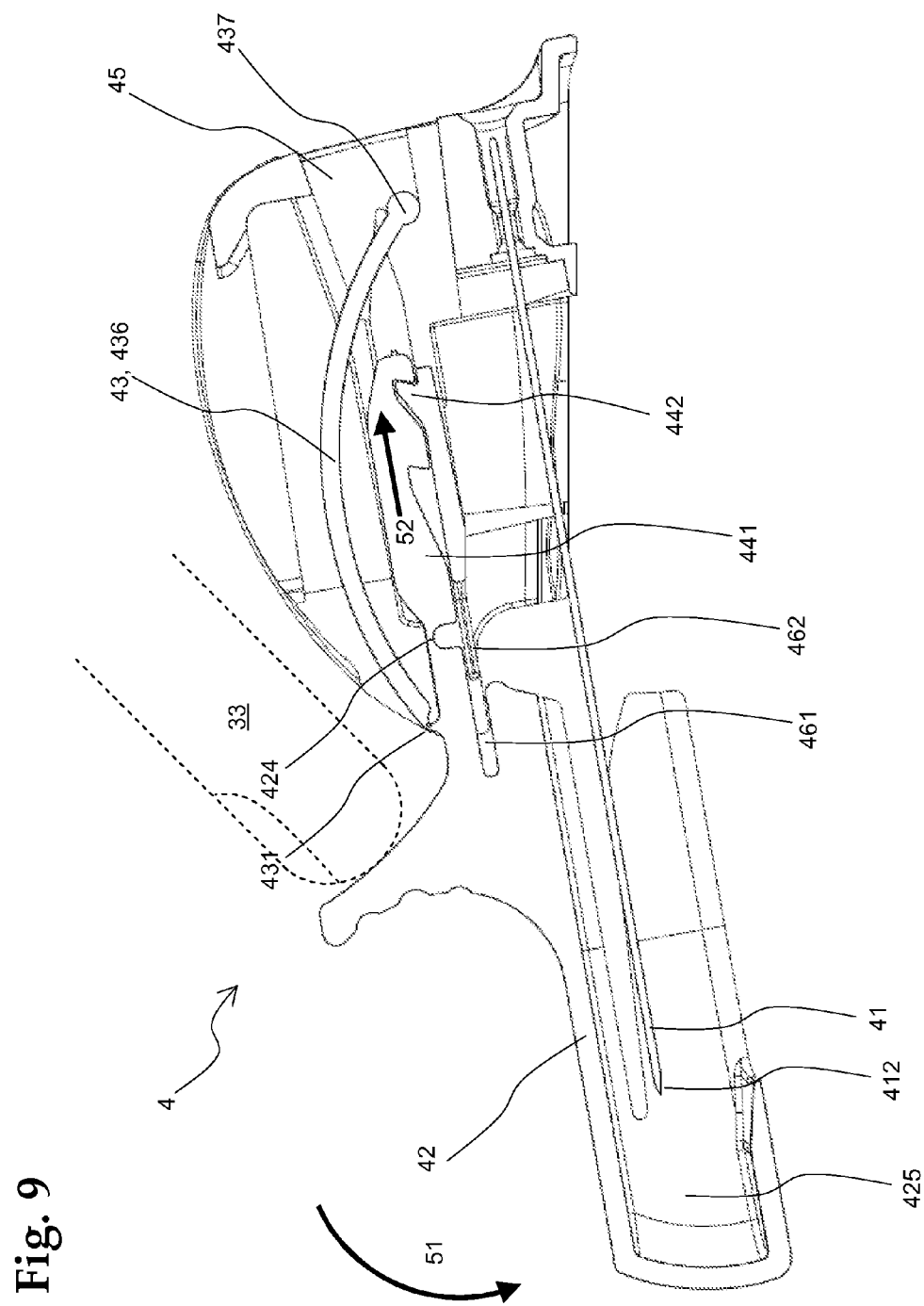
FIG. 9 illustrates the device of FIG. 6 after having been removed from the installed infusion site interface and with the needle cover pivoted back into the first position according to an embodiment of the present disclosure.

To safely dispose the insertion device 4 with the now exposed insertion needle 41, the user can now pivot the needle cover 42 back over the needle 41, arriving back at the first position as shown in FIG. 9. However, in contrast to the state of the device in FIG. 2, where the spring element 43 in its first configuration is unbiased, the spring element 43 in its second configuration can now be elastically deformed and biased and can exert a force.

Figure 5:
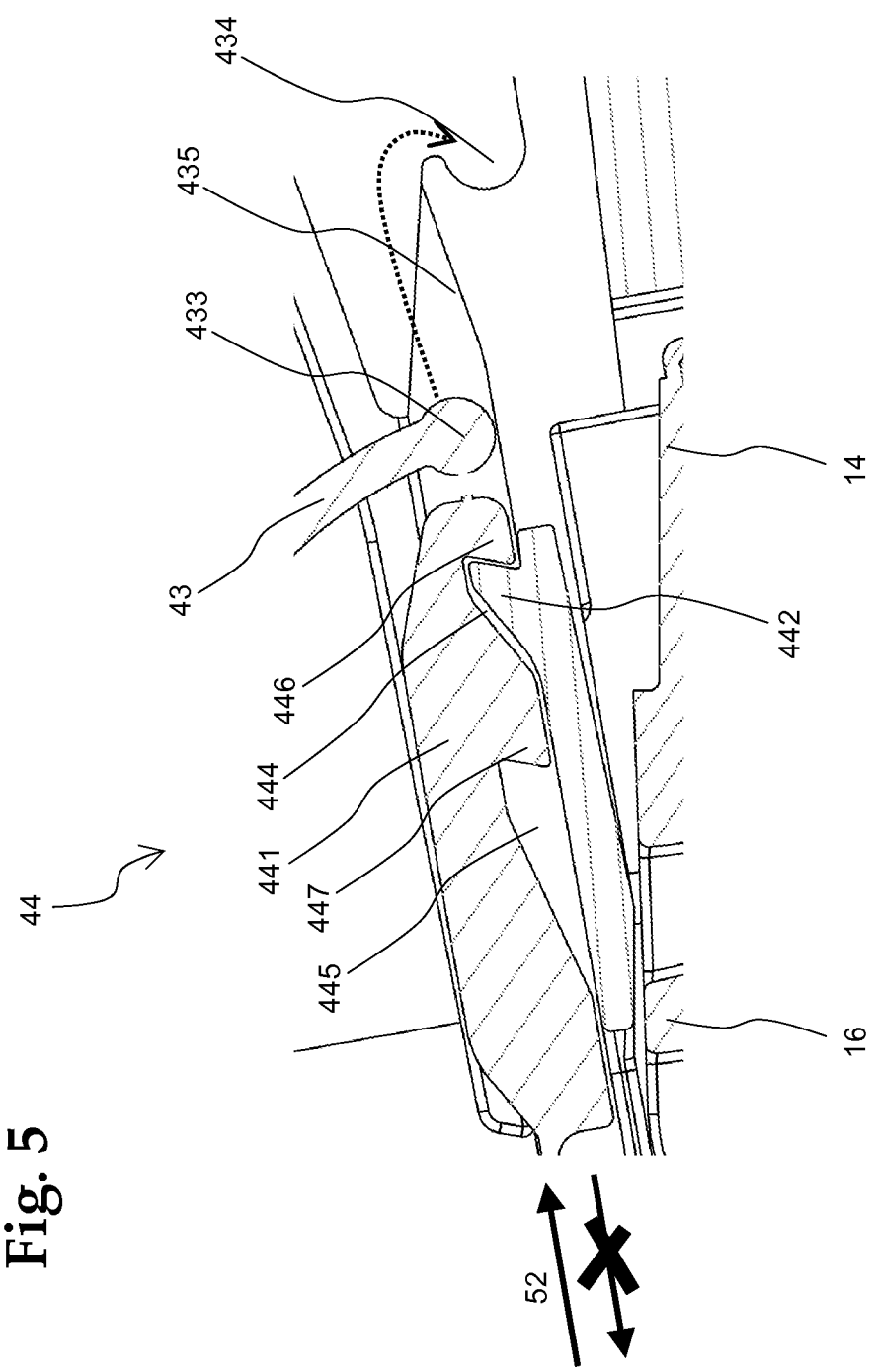
FIG. 5 illustrates a detail view of the device in FIG. 2 in the area of the translational lock mechanism according to an embodiment of the present disclosure.

The translational lock 44 and the rotational lock 46 are now explained in more detail, by referring back to FIG. 3, where a detailed view is given of the rotational lock mechanism 46, and to FIG. 5, where a detailed view is given of the translational lock 44.

The rotational lock 46 can comprise a tongue 462 connected to the handle structure 45 and a slot 461 in the needle cover 42. As long as the needle cover 42 is in the first position of FIG. 2, the tongue 462 can be located outside of the slot 461 and the rotational movement 51 of the needle cover 42 around the pivotal point 424 cannot be hindered. In FIG. 9, however, a spring force can be directed toward the handle structure 45 (to the right in FIG. 9). Therefore, in the moment the needle cover 42 reaches the first position, the sliding element 41 can shift from the left to the right along translational direction 52 and the tongue 462 can lock to the slot 461, thereby establishing the rotational lock 46. The needle cover 42 can no longer pivot 51 back to its second position. This becomes clearer in the detailed view provided in FIG. 11, where the tongue 462 has reached its final position in the lock mechanism 46. The needle cover 42 of the device 4 can now be locked in a position where the needle 41 can be located within the needle cover 42. Since the needle 41 is no longer exposed, the device 4 can now be safely disposed.

Figure 3:
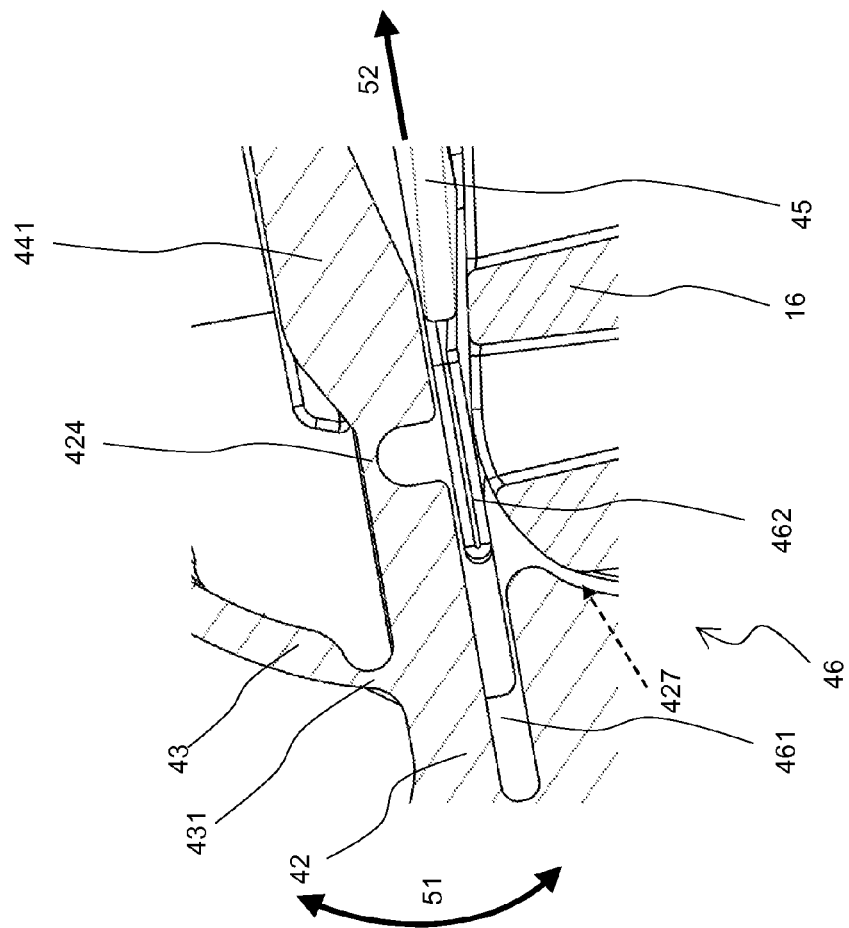
FIG. 3 illustrates a detail view of the device in FIG. 2 in the area of the rotational lock mechanism according to an embodiment of the present disclosure.

An additional advantageous effect of the tongue 462 can be the fact that it can interact with the curved area 427 of the side walls of the needle cover 42 marked by a dashed arrow in FIGS. 2 and 3. As long as the needle cover 42 is not yet back in its first position, the tip of the tongue 462 can slide on the area 427, thereby blocking the movement of the sliding element 441 along direction 52. This feature can provide that the locking mechanisms 44, 46, 46' may not be prone to jamming, since the locking mechanisms 44, 46, 46' can become functional only when the needle cover 42 reaches the first position.

An alternative, or additional, rotational lock 46' is shown in FIGS. 12A and 12B. The portion of the needle cover 42 close to the hinge 424 can be mounted in a guiding slot 463. In the first position (FIG. 12A), corresponding to FIG. 2, the living hinge 424 can be located outside of the guiding slot 463 of the rotational lock 46'. The needle cover 42 can carry out its pivotal motion. Then, driven by the spring force of the spring element 43, the sliding element 441 can be shifted to the right along translational direction 52. The hinge 424 and the adjacent region 426 of the cover 42 can now be located in the slot 463. As a result, the rotational motion 51 can be blocked.

Figure 11:
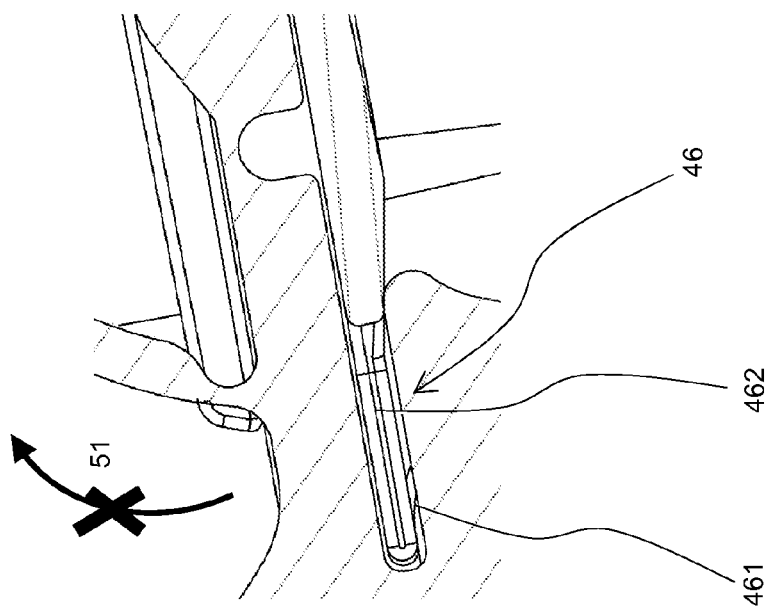
FIG. 11 illustrates a detail view of the device in FIG. 10 in the area of the first rotational lock mechanism according to an embodiment of the present disclosure.

A device 4 can be provided with one or both of the rotational lock mechanisms 46, 46' depicted in FIGS. 11 and 12. An embodiment with both rotational locks 46, 46' can be advantageous, since in such a configuration the two portions of the device 4 that are subject to mechanical stress can have a certain distance to each other along direction 52. This can strongly increase the overall mechanical strength of the rotational lock.

Figure 13:
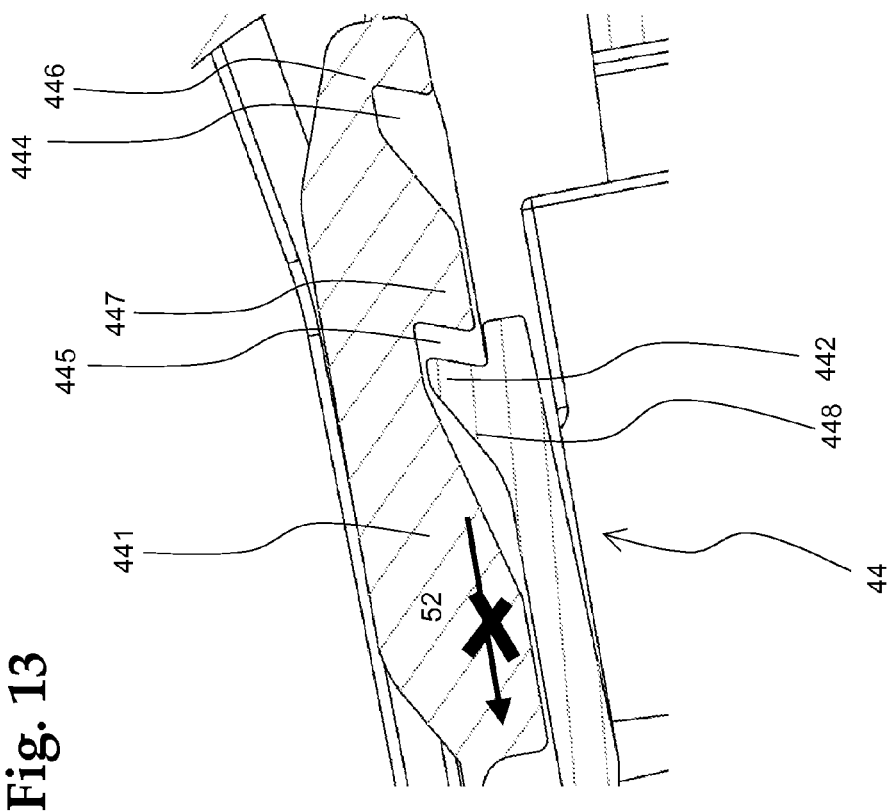
FIG. 13 illustrates a detail view of the device in FIG. 10 in the area of the translational lock mechanism according to an embodiment of the present disclosure.

In one embodiment, an additional lock mechanism 44 can be provided as a linear ratchet mechanism comprising a linear rack and a pawl. As can be seen in FIGS. 5 and 13, the linear rack can be the sliding element 441. A pawl 442 can be spring-loadedly mounted on the handle structure 45, interacting with the teeth 446, 447 of the linear rack element 441, which can be guided in the guiding slot. The main purpose of the translational lock 44 can be to irreversibly lock the sliding element 441 in a position where the rotational lock(s) 46, 46' are established, thereby permanently locking the needle cover 42 in its third, final position.

The translational lock 44 can essentially be in two states. In a first state (corresponding to the FIG. 5), the pawl 442 can be positioned in the first groove 444 of the rack element 441. This is the case in FIGS. 2 to 9. The sliding element 441 cannot shift to the left, away from the handle structure 45, since the undercut first tooth 446 of the sliding element 441 can hook into the undercut pawl 442.

Figure 10:
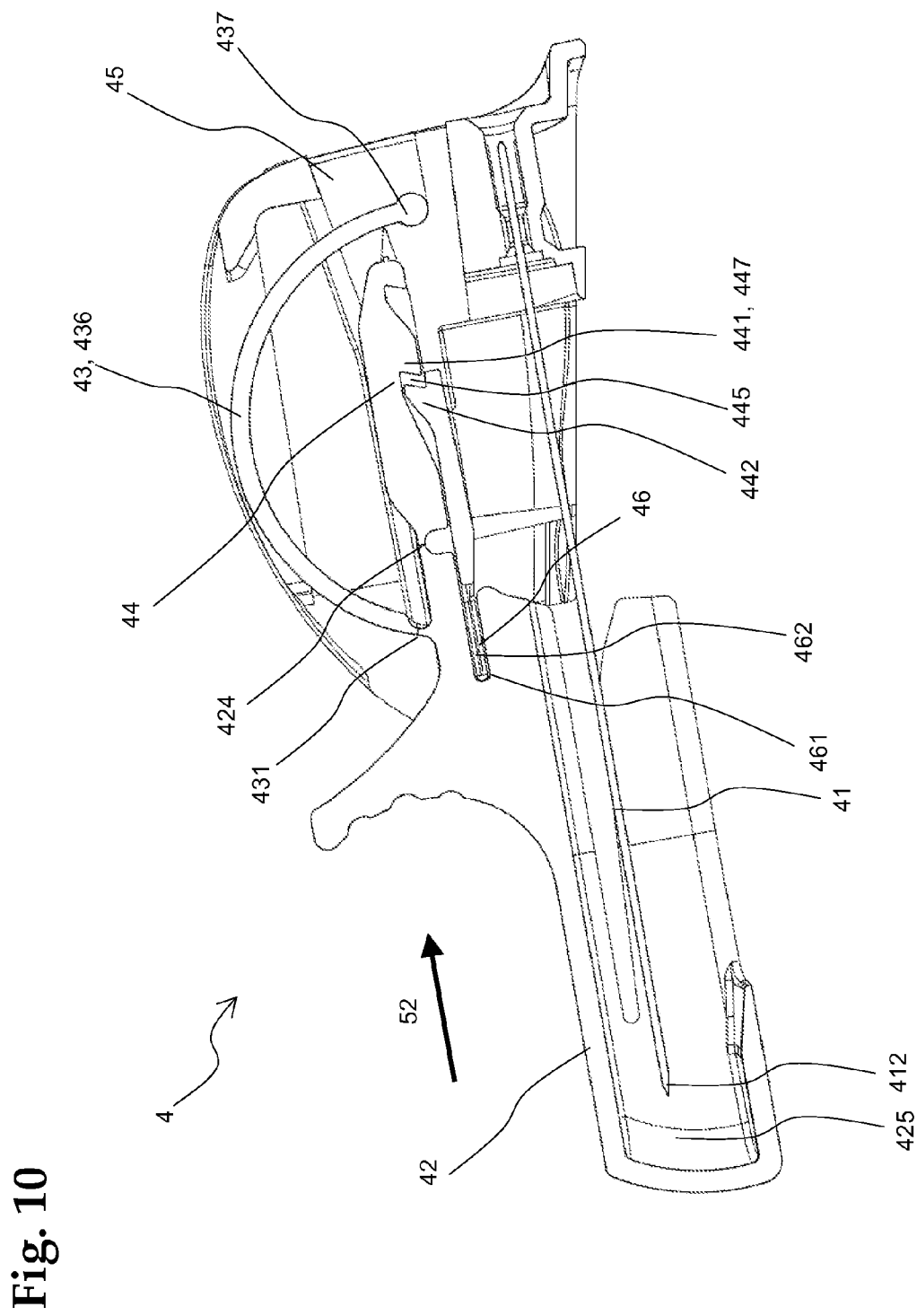
FIG. 10 illustrates the device of FIG. 9 with the needle cover irreversibly and permanently locked in a third, final position according to an embodiment of the present disclosure.

Driven by the tension of the spring element 43 in its new, second configuration (see FIG. 9), the sliding element 441 can shift to the right along translational direction 52. The ramp 448 of the pawl 442 can glide over the second tooth 447, finally arriving in the situation of FIG. 13, where the pawl 442 can now be positioned in the second groove 445. The undercut second tooth 447 of the sliding rack element 441 can hook into the undercut pawl 442. The linear ratchet mechanism 44 can be permanently locked. The needle cover 42 of the device 4 can also be shifted to the right and can now be in its final, third position, as it is shown in FIG. 10. The tip 412 of the insertion needle 41 can inaccessibly be located in the closed cap 425 in the front of the needle cover 42.

In an alternative embodiment, the roles of the sliding rack element 441 and the pawl 442 can be exchanged, the pawl 442 being a part of the sliding element 441 and the linear rack being part of the handle frame 45. It can also be possible to spring-load the linear rack instead of the pawl 442, or even both elements.

It should be mentioned that the insertion device 4 can have the further advantage that it cannot be possible for the needle cover 42 to lock into the third position as long as the device 4 is still mounted on an infusion site interface 1. Referring back to FIGS. 2 and 3, one can see that the shape of the needle cover 42 in the area 427 marked by a dashed arrow corresponds to the shape of the body 16 of the infusion site interface 1. As a consequence, if the user erroneously pivots the needle cover 42 back to its first position before he has inserted the needle 41 and cannula 12, which may be possible, the marked area of the needle cover 42 can rest on the adjacent interface body 16, thereby rendering the lock mechanisms 44, 46, 46' non-functional, as the needle cover 42 cannot shift along direction 52. The user cannot accidentally lock the needle cover 42 prior to use and make the device 4 irreversibly non-functional.

A device 4 can also be realized without a rotational lock mechanism 46, 46'. If no rotational lock is provided, the needle cover 42 nevertheless cannot expose the needle 41. Due to the translational lock mechanism 44, the needle tip 412 can be shifted into the fully closed cap 425 of the needle cover 42 and the front end of the needle 41 can collide with the cap 425, thereby also preventing the needle 41 from leaving the needle cover 42.

The functionality of the device 4 will now be summarized and described FIGS. 14A-D. For a better understanding, only the features of the device 4 that explain the basic functionality are shown.

In FIG. 14A, the device 4 is shown with the needle cover 42 in the first position. The spring element 43 can be in the first, non-functional configuration. The needle cover 42 can then be pivoted 51 about the cover hinge 424 into its second position, as shown in FIG. 14B. The needle 41 can be exposed and can be inserted into the body of the patient. The pawl 433 of the spring element 43 can snap into groove 434, thereby establishing the second hinge 437 of the spring element 43. The spring element 43 can now be in its second, functional configuration.

After having removed the device 4 from the interface 1, the needle cover 42 can be pivoted back to the first position, arriving at FIG. 14C. The spring element 43 can generate a force that actuates the needle cover 42 with sliding element 441 along direction 52. The sliding element/linear rack 441 can be shifted along 52 and the pawl 442 can hook into the second tooth of the linear rack 441. The needle cover 42 can now be in the third position, as shown in FIG. 14D. The cover hinge 424 can be located within the guiding slot 463 and can no longer be functional. The sliding element 441 can be locked by the ratchet mechanism 44. As a result, the needle cover 42 can be permanently locked in its rotational position in regard to the handle 45 and the needle tip can be located in the cap 425. The device 4 can now be safely disposed.

The embodiments of an insertion device 4 and an infusion site interface 1 that have been discussed so far are for subcutaneous infusion, such as, for example, in combination with an infusion pump system. However they can also be used for intravenous infusions, with some minor adaptations to the infusion site interface. As already mentioned above, the device 4 can also be applied for inserting sensors into a body of a patient, instead of a soft cannula 12.

Figure 15:
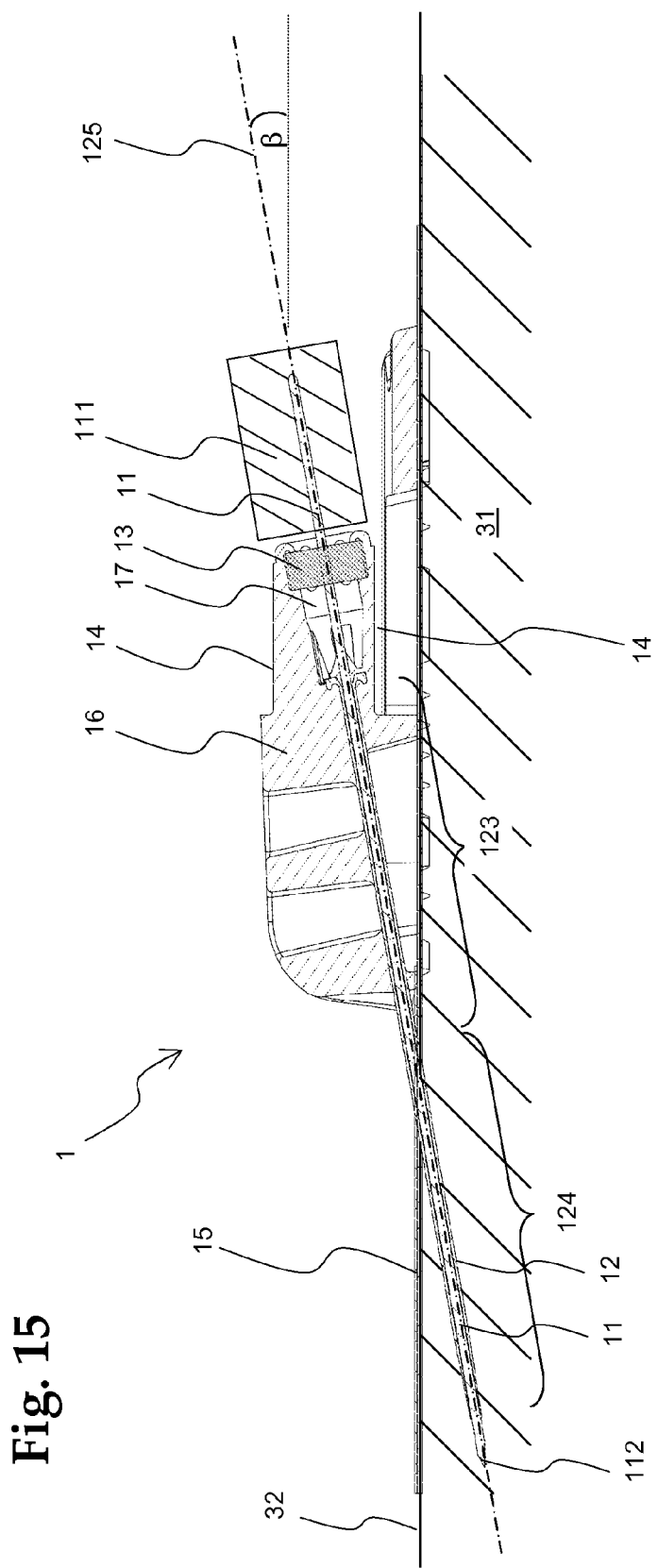
FIG. 15 illustrates a cross-section through an infusion site interface after insertion of the infusion cannula according to an embodiment of the present disclosure.
Figure 16:
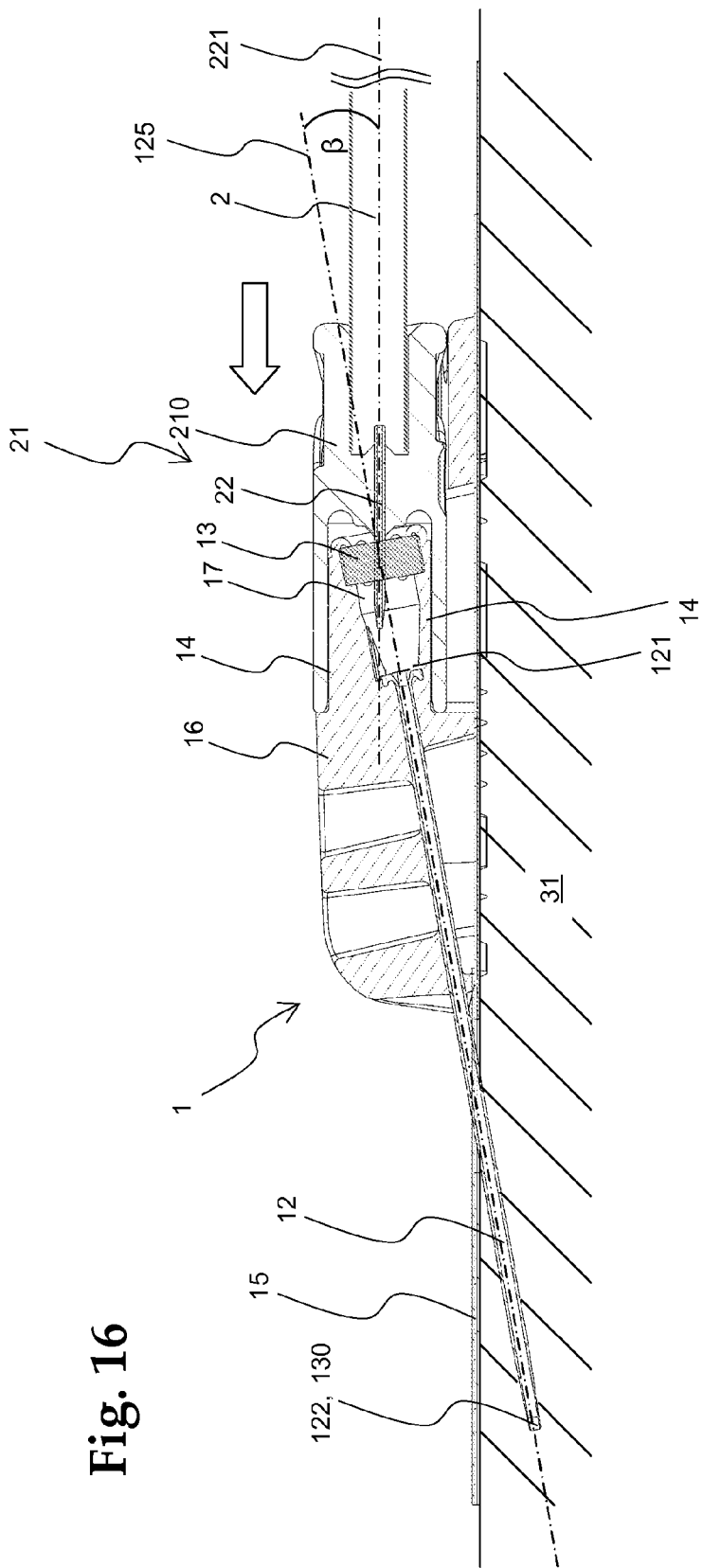
FIG. 16 illustrates a cross-section through an infusion site interface after removal of the insertion needle and with established fluid connection to infusion tubing according to an embodiment of the present disclosure.

One embodiment is shown in FIGS. 15 and 16. FIG. 15 shows a cross-section through the infusion site interface 1 attached to the body of a patient, directly after insertion of the infusion cannula 12, while FIG. 16 shows the infusion site interface 1 after the insertion needle 11 has been removed and the infusion tubing 2 has been connected to the interface 1.

The shown infusion site interface 1 can comprise an interface body 16 mounted on an adhesive pad 15 for attaching the interface to the skin 32 of a patient. An infusion cannula 12 can be arranged at an acute angle β to the pad 15. The angle β can be around 10 degrees, but this mainly depends on the particular design of the interface. One part 123 of the cannula 12 can be mounted in the interface body 1, and the other part 124 can project to the adhesive side of the pad 15 through an opening in the pad. A first end 121 of the cannula 12 can open toward a cavity 17 in the interface body 16, the cavity 17 can be sealed closed by a septum 13. An insertion needle 11 can be in the cannula 12 and the septum 13. The septum 13 can be mounted in the interface body 16 such that its surface can be substantially perpendicular to the longitudinal axis 125 of the cannula 12.

A difference of the shown embodiment of an interface in regard to the prior art interface as shown in FIG. 1A is the guide 14 on the interface body 16. The guide 14 can guide a connector 21 of the infusion tubing 2 with its hollow needle 22 parallel to the plane defined by the pad 15.

As can be seen in FIG. 16, a connector 21 fluidly connected to the infusion site interface 1 can comprise a connector body 210 and a second guide 211. The second guide 211 can interact with the guide 14 of the interface body 16. The connector 21 can comprise a hollow needle 22 that can penetrate the septum 13 of the interface 1. The needle 22 can be collinear with the tubing 2 adjacent to the connector body 210. When a user couples the connector 21 to the interface 1, the guide 14, interacting with the second guide 211, can guide the connector 21 and the hollow needle 22 parallel to the plane defined by the pad 15. As a result, the hollow needle 22 can penetrate the septum 13 at angle β to its perpendicular 130.

Due to the guide 14, the coupled connector 21 can be mounted horizontal on the interface body 16, with a substantially flat overall surface of interface body 16 and connector body 210. The tubing 2 adjacent to the connector can leave the connector parallel to the pad 15 and thus to the skin surface of the patient. Such an infusion site interface 1 can provide a low profile and smooth surface with a considerably lower risk of getting caught on clothing or the like.

It can be possible to apply adhesive tape, or an additional adhesive pad, to cover a part of or even the complete infusion site interface with coupled connector in order to achieve a smooth surface. This can further decrease the risk of ripping the cannula out of the patient's body or the inadvertently disconnecting the infusion site interface from the infusion tubing. Yet another advantage of such an additional cover can be the possibility to camouflage the complete infusion site interface by using a skin colored adhesive pad. In contrast, covering a prior art infusion site interface with coupled connector as shown in FIG. 1B with tape would be rather unadvisable since the connector would be subject to shearing forces that could detach the interface from the skin, and could destroy the connection.

The embodiment shown in FIGS. 15 and 16 represents one possible arrangement of the cannula axis, the connector needle axis, and the axis of the septum. Other possible layouts of an infusion site interface 1 are shown in FIGS. 17A to D. For a better understanding, only certain components for explaining the different embodiments are shown.

Figure 17A:
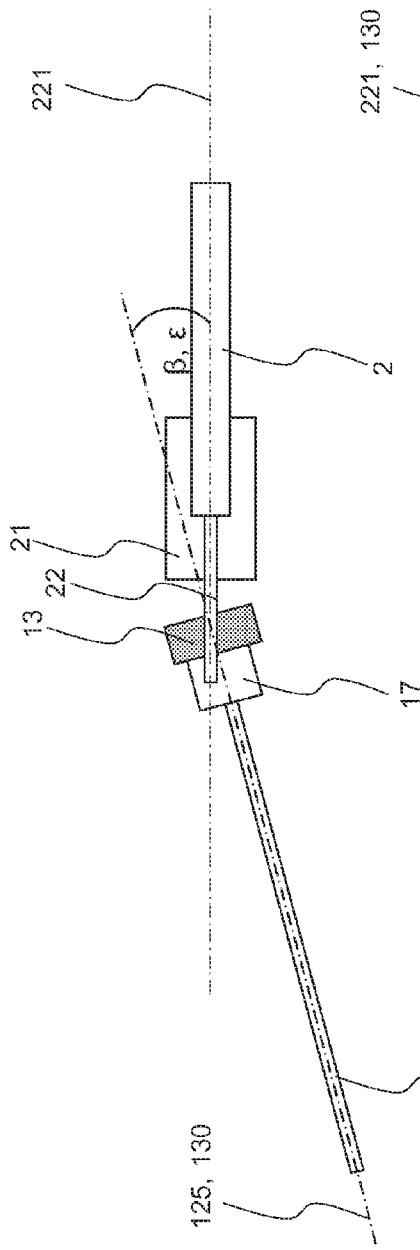
FIGS. 17A-D schematically illustrates the arrangement of the various axes in four possible variants of an infusion site interface according to an embodiment of the present disclosure.

FIG. 17A schematically shows the embodiment shown in FIGS. 15 and 16. As in all of FIG. 17, the axis 221 of the hollow needle 22 of the connector 21 can be arranged substantially parallel to the plane defined by the adhesive pad (not shown) of the. An infusion cannula 12 can be arranged with its axis 125 at an angle β to axis 221. The axis 130 of the septum 13 can be substantially parallel to the cannula axis 125. The angle between axis 130 and pad plane/axis 221 can be denominated ε.

Figure 17B:
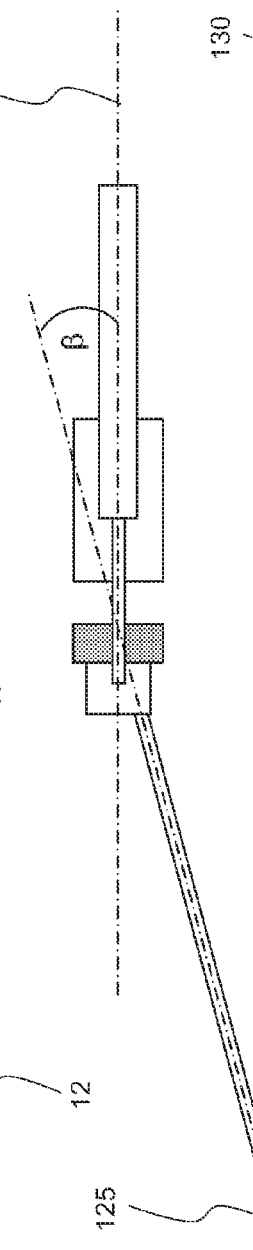

FIG. 17B shows another embodiment, in which the axis 130 of the septum can be substantially parallel to the hollow needle axis 221, and thus angle ε can be zero degrees. In contrast to FIG. 17A, the insertion needle (not shown) arranged in the cannula 12 can penetrates the septum surface at an angle β while the hollow needle 22 can penetrate the septum substantially perpendicularly (ε=0).

Figure 17C:
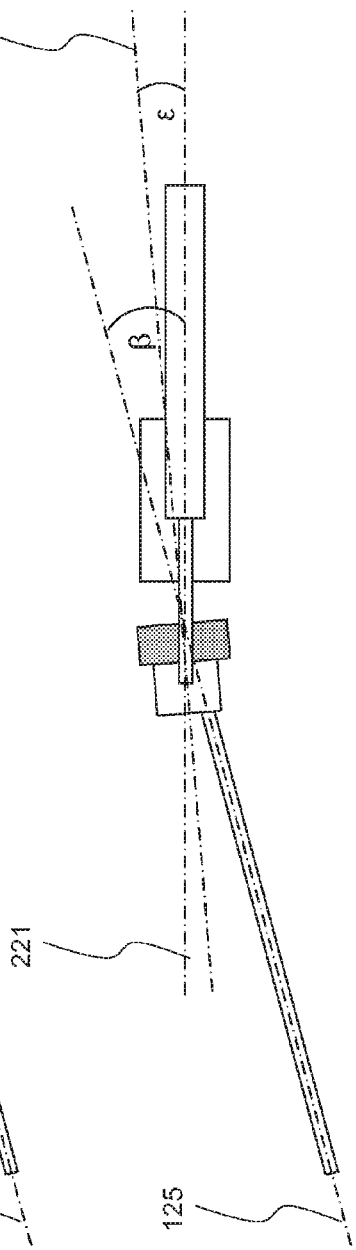

A further embodiment is shown in FIG. 17C, where the angle ε is chosen smaller than the angle β. As a result, both the insertion needle (not shown) as well as the hollow needle 22 can penetrate the septum 13 at an angle. This tilted arrangement of the septum 13 in regard to both axes 125 and 221 can have the advantage that the maximum deviation from the septum axis 130 can be smaller than in FIGS. 17A and B.

Figure 17D:
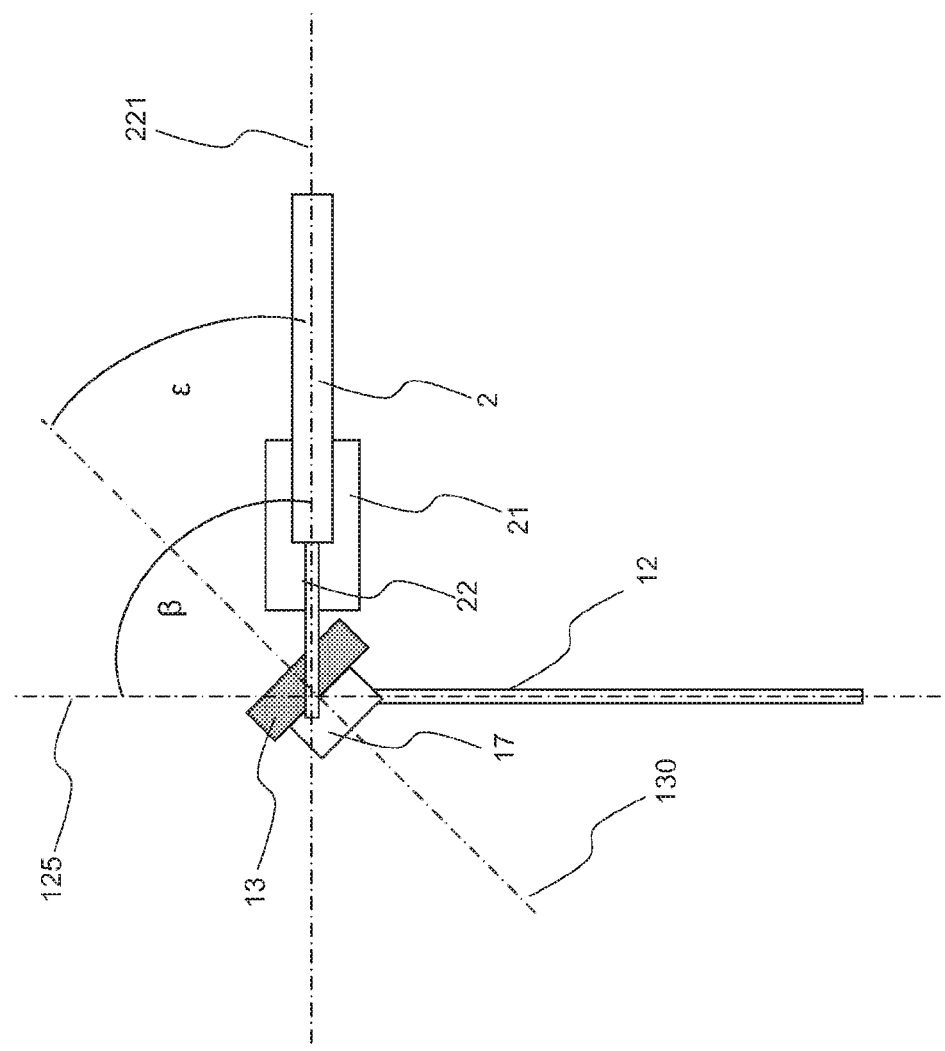

FIG. 17D discloses an embodiment in which such an arrangement can be advantageous. The cannula 12 can be arranged substantially perpendicularly to the pad 15 of the device 4 and thus can be substantially perpendicular to the skin surface (β=90 degrees). On the other hand, the hollow needle 22 of the connector 21 can still parallel to the plane defined by the pad (not shown). The septum 13 can be arranged such that its axis 130 can have an angle ε approximately equal to 45 degrees. Thus both the insertion needle 11 and the hollow needle 22 can penetrate the septum 13 at an angle of about 45 degrees to its perpendicular 130.

Therefore the present disclosure provides a device for inserting a soft cannula or a sensor into the body of a patient that can be safely disposed after use without the need of special needle disposal containers; a device for inserting a soft cannula or a sensor into the body of a patient, an infusion site interface together with such a device, and a sensor site interface together with such a device that allows safe handling prior to use and during the insertion of the cannula or sensor; an insertion device that comprises safeguards against incorrect operation by a user; an infusion site interface that can be safely coupled to an infusion tubing with a decreased risk of parts of the interface or a tubing connector getting caught on obstacles. Such an infusion site interface should have a small overall height.

The insertion devices and infusion site interfaces can be producible at low costs. Advantageously such insertion devices can be compatible with existing types of infusion site interfaces. Furthermore infusion site interfaces can be compatible with existing types of connectors for infusion tubing.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

The invention claimed is:

1. An infusion site interface, the infusion site interface comprising:
    an interface body mounted on a pad that is configured to adhesively attach to a body of a patient;
    a soft infusion cannula configured for insertion into the body of the patient, wherein the infusion cannula is connected to the interface body;
    wherein the interface body defines a cavity fluidly connected to the infusion cannula;
    a septum that seals closed the cavity, wherein the septum has a substantially planar surface positioned opposite the cavity, wherein the septum is penetrable by an insertion needle in the infusion cannula, in a first angle to a perpendicular of the planar surface of the septum, and is penetrable by a hollow needle of an infusion tubing connector coupled to the infusion site interface, in a second angle to the perpendicular of the planar surface of the septum, wherein the same planar surface is configured to be pierced by the insertion needle and the hollow needle; and
    a guide configured to guide the hollow needle of the infusion tubing connector during coupling, parallel to a plane defined by the pad, wherein the infusion tubing connector engages the guide in a horizontal direction that is parallel to the plane defined by the pad, wherein the horizontal direction defines the second angle that is different from the first angle.

2. The infusion site interface according to claim 1, wherein an insertion needle is removably arranged in the infusion cannula and penetrates the septum.

3. The infusion site interface according to claim 1, further comprising:
    an insertion device for inserting the infusion cannula into a body of a patient, the device comprising:
        an insertion needle adapted to be removably arranged in the infusion cannula of the infusion site interface;
        a handle structure connected to the insertion needle; and
        a needle cover, wherein the needle cover is pivotably mounted on the handle structure and is rotatably movable between a first position, where a front part of the insertion needle is located in the needle cover, and a second position, where the front part of the insertion needle is exposed.

4. The infusion site interface according to claim 3, wherein the needle cover of the insertion device comprises a longitudinal slot arranged such that the front part of the insertion needle passes through the slot when the needle cover is pivoted.

5. The infusion site interface according to claim 3, wherein a spring element actuates the needle cover of the insertion device toward the second position.

6. The infusion site interface according to claim 3, wherein a spring element in a first configuration is not functional and in a second configuration actuates the needle cover of the insertion device toward the second position, wherein the spring element irreversibly changes from its first configuration to its second configuration when the needle cover arrives at the second position for the first time.

7. The infusion site interface according to claim 6, wherein the spring element comprises a pawl that irreversibly snaps into a groove in the handle structure of the insertion device when the needle cover of the insertion device arrives at the second position, thereby establishing a second hinge between the spring element and the handle structure.

8. The infusion site interface according to claim 6, wherein the spring element comprises an elastic bar connected on one end with the needle cover of the insertion device by a first hinge and connected on the other end with the handle structure of the insertion device by a second hinge.

9. The infusion site interface according to claim 3, wherein the needle cover of the insertion device comprises an element slidably mounted on the handle structure of the insertion device, such that the needle cover with the sliding element is linearly movable between the first position and a third position.

10. The infusion site interface according to claim 3, wherein the insertion device further comprises one or more lock mechanisms for locking the needle cover in a position where the insertion needle is located within the needle cover.

11. The infusion site interface according to claim 3, wherein the needle cover of the insertion device comprises an element slidably mounted on the handle structure of the insertion device and linearly movable between the first position and a third position, and a rotational lock mechanism realized as a slot-tongue joint, wherein a slot is on the needle cover and the tongue is on the sliding element or vice versa, and wherein the slot and the tongue do not engage when the sliding element is in one position and do engage when the sliding element is in the other position, thereby blocking the rotational motion of the needle cover and establishing a lock of the needle cover.

12. The infusion site interface according to claim 3, wherein the needle cover of the insertion device comprises an element slidably mounted on the handle structure of the insertion device and linearly movable between the first position and a third position, and a rotational lock mechanism comprising a guiding slot, wherein a hinge of the needle cover is located outside the guiding slot when the sliding element is in one position and is located inside the guiding slot when the sliding element is in the other position, thereby blocking the rotational motion of the needle cover by making the hinge non-functional and establishing a lock of the needle cover in the first position.

13. The infusion site interface according to claim 3, wherein the needle cover of the insertion device comprises an element slidably mounted on the handle structure of the insertion device, such that the needle cover with the sliding element is linearly movable between the first position and a third position, and a translational lock mechanism realized as a linear ratchet mechanism, wherein the sliding element acts as a linear rack element of the linear ratchet mechanism and the handle structure comprises a spring-loaded pawl of the linear ratchet mechanism or vice versa.

14. The infusion site interface according to claim 3, wherein the needle cover of the insertion device comprises two parallel slots in sidewalls of the needle cover.

15. An infusion set with an infusion site interface according to claim 1.

16. An infusion pump system with an infusion site interface according to claim 1.

17. An infusion site interface, the infusion site interface comprising:
an interface body mounted on a pad that is configured to adhesively attach to a body of a patient;
a soft infusion cannula configured for insertion into the body of the patient, wherein the infusion cannula is connected to the interface body;
wherein the interface body defines a cavity fluidly connected to the infusion cannula, wherein the cavity has an opening;
a septum that seals closed the cavity, wherein the septum has a substantially planar surface that spans across the opening of the cavity to seal the opening of the cavity, wherein the planar surface of the septum is penetrable by an insertion needle in the infusion cannula, in a first angle to a perpendicular of the planar surface of the septum, and wherein the same planar surface of the septum is penetrable by a hollow needle of an infusion tubing connector coupled to the infusion site interface, in a second angle to the perpendicular of the planar surface of the septum, wherein the infusion tubing connector engages a guide in a horizontal direction that is parallel to the plane defined by the pad, wherein the horizontal direction defines the second angle that is different from the first angle; and
the guide is configured to guide the hollow needle of the infusion tubing connector during coupling, parallel to a plane defined by the pad.

18. The infusion site interface according to claim 17, wherein an insertion needle is removably arranged in the infusion cannula and penetrates the septum.

19. The infusion site interface according to claim 17, further comprising:
an insertion device for inserting the infusion cannula into a body of a patient, the device comprising:
an insertion needle adapted to be removably arranged in the infusion cannula of the infusion site interface;
a handle structure connected to the insertion needle; and
a needle cover, wherein the needle cover is pivotably mounted on the handle structure and is rotatably movable between a first position, where a front part of the insertion needle is located in the needle cover, and a second position, where the front part of the insertion needle is exposed.

20. The infusion site interface according to claim 19, wherein the needle cover of the insertion device comprises a longitudinal slot arranged such that the front part of the insertion needle passes through the slot when the needle cover is pivoted.

21. The infusion site interface according to claim 19, wherein a spring element actuates the needle cover of the insertion device toward the second position.

22. The infusion site interface according to claim 19, wherein a spring element in a first configuration is not functional and in a second configuration actuates the needle cover of the insertion device toward the second position, wherein the spring element irreversibly changes from its first configuration to its second configuration when the needle cover arrives at the second position for the first time.

23. The infusion site interface according to claim 19, wherein the needle cover of the insertion device comprises an element slidably mounted on the handle structure of the insertion device, such that the needle cover with the sliding element is linearly movable between the first position and a third position.

\* \* \* \* \*